United States Patent [19]

Plattner

[11] 4,389,416
[45] Jun. 21, 1983

[54] DIPHENYL ETHER, DIPHENYL THIOETHER AND DIPHENYL METHANE PHENOL MANNICH BASES

[75] Inventor: Jacob J. Plattner, Libertyville, Ill.

[73] Assignee: Abbott Laboratories, North Chicago, Ill.

[21] Appl. No.: 310,164

[22] Filed: Oct. 9, 1981

[51] Int. Cl.³ .................. A61K 31/215; C07C 101/30; C07C 103/29; C07C 91/16

[52] U.S. Cl. .................................... 424/309; 424/319; 424/324; 424/330; 560/9; 560/12; 560/13; 560/17; 560/36; 560/42; 562/426; 562/430; 562/431; 562/451; 564/162; 564/165; 564/306; 564/348; 562/441

[58] Field of Search .................... 560/9, 12, 13, 42, 17, 560/36; 564/162, 165, 306, 348; 424/309, 324, 330, 319; 562/426, 431, 441, 430, 451

[56] References Cited

U.S. PATENT DOCUMENTS 4,106,925  8/1978  Rohr et al. .......................... 560/9 X
4,156,011  5/1979  Lafon et al. ........................ 424/309

*Primary Examiner*—Natalie Trousof
*Assistant Examiner*—Vera C. Clark
*Attorney, Agent, or Firm*—Gildo E. Fato; Robert L. Niblack

[57] ABSTRACT

Described are compounds of the formula

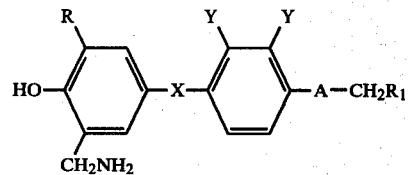

wherein R is hydrogen, loweralkyl, aminomethyl or halo; $R_1$ is carboxy, carboxyloweralkyl, aminocarbonyl, hydroxymethyl, anilinomethyl, or aminomethyl; A is oxygen, $CH_2$, Sulfur or a single bond; X is oxygen, $CH_2$, sulfur or sulfoxide; and Y is hydrogen, loweralkyl or halo and may be the same or different, and pharmaceutically acceptable salts thereof.

The compounds are effective as diuretic agents.

30 Claims, No Drawings

DIPHENYL ETHER, DIPHENYL THIOETHER AND DIPHENYL METHANE PHENOL MANNICH BASES

BACKGROUND OF THE INVENTION

The present invention provides compositions for the treatment of hypertension, edema, cardiac failure, and other conditions involving fluid and electrolyte accumulation. A diuretic composition in dosage unit form is described.

SUMMARY OF THE INVENTION

The present invention is directed to compounds of the formula

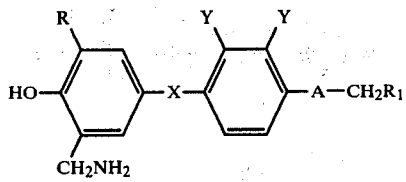

wherein R is hydrogen, loweralkyl, aminomethyl or halo; $R_1$ is carboxy, carboxyloweralkyl, aminocarbonyl, hydroxymethyl, anilinomethyl, or aminomethyl; A is oxygen, $CH_2$, sulfur or a single bond; X is oxygen, $CH_2$, sulfur or sulfoxide; and Y is hydrogen, loweralkyl or halo and may be the same or different, and pharmaceutically acceptable salts thereof.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methyl-hexyl, n-pentyl, 1-methylbutyl, 2,2-dimethyl-butyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg./kg. per day per patient are useful, with the total dose of up to 1 gm. per day being a suitable range for large animals, including humans. The whole dosage range described increases the total urinary excretion from about 2 to about 10-fold in most animals. From these figures, it is apparent that the new diuretic compounds are particularly effective in increasing urinary excretion in most animals.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

The diphenyl ethers and diphenyl thioethers described in this invention were prepared according to the reaction sequence shown below (SCHEME I). Although this reaction sequence illustrates the synthesis of the dichloro compounds, other compounds of the invention can be made in the same manner using the appropriate starting materials.

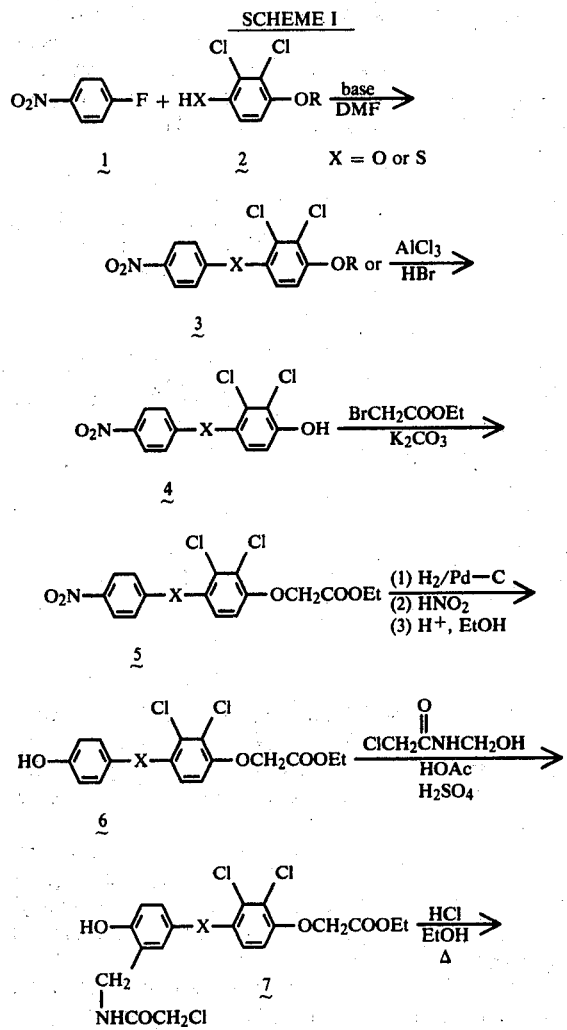

-continued
SCHEME I

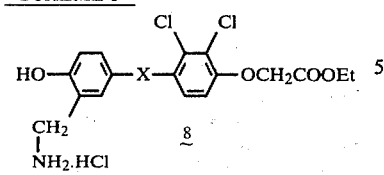

Condensation of p-fluoronitrobenzene (1) with the appropriate substituted alkoxy benzene (2) in the presence of base gave the ether or thioether (3). The alkoxy group in (3) was cleaved using either aluminum chloride or hydrobromic acid. The resulting phenol (4) was then alkylated with ethyl bromoacetate in the presence of anhydrous potassium carbonate to give the substituted phenoxyacetic ester (5). Replacement of the nitro function in (5) by hydroxyl was accomplished by catalytic reduction to the aniline derivative followed by diazotization and heating the resulting diazonium salt in aqueous $H_2SO_4$. The desired phenolic ester (6) was obtained after esterification with ethanol/sulfuric acid. Amidoalkylation of (6) in a mixture of acetic and sulfuric acid led to adduct (7). Acid hydrolysis of the chloroacetyl group in (7) then gave the desired final product (8) as the hydrochloride salt.

To prepare the diphenylmethane derivatives (11), the previously described benzophenone (9) was allowed to react with sodium borohydride in trifluoroacetic acid as shown below to give (10). Elaboration of compound (10) to final product (11) was effected by an analogous set of reactions as depicted in SCHEME I.

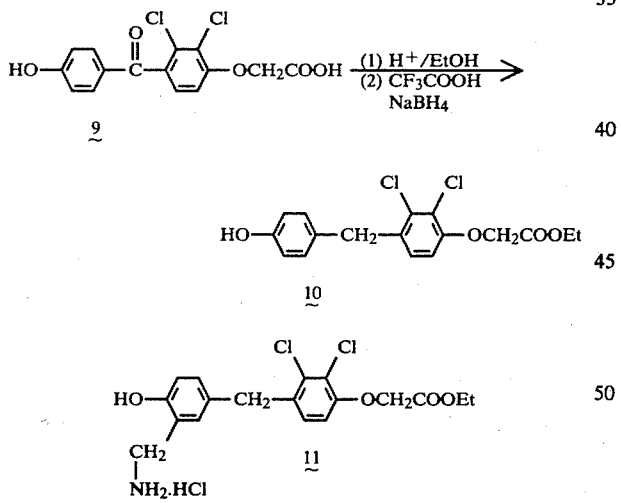

Carboxamide derivatives described in this invention were prepared from the aminoesters by first blocking the amino function with a CBZ or t-BOC group, displacing the ester with ammonia and then deblocking the amine with acid.

The substituted phenoxyethanol compounds described in this invention were prepared by reducing the intermediate (7) (in SCHEME I) with sodium borohydride and then continuing with the last step as indicated in SCHEME I.

Ortho-chlorophenols described in this invention were obtained by chlorinating the phenols with sulfuryl chloride in 1,2-dichloroethane as the solvent.

SCHEME 2

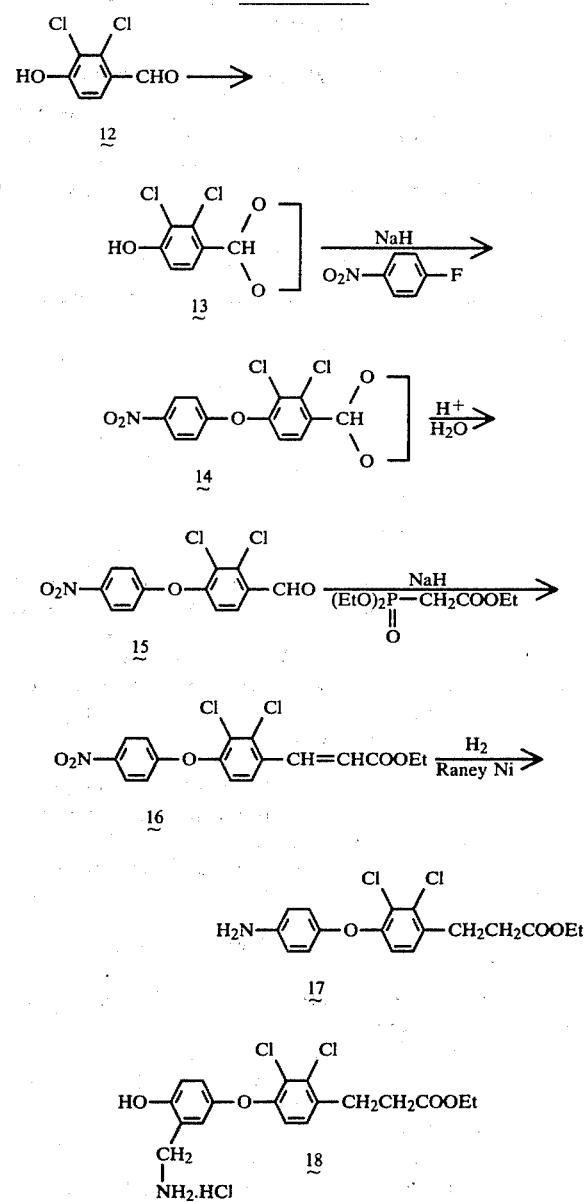

To prepare the substituted phenylpropionic ethyl esters of type (18), 2,3-dichloro-4-hydroxybenzaldehyde (12) was converted to the acetal (13) with ethylene glycol in refluxing benzene. This compound was allowed to react with p-fluoronitrobenzene in the presence of NaH to give the diphenyl ether (14). Deacetalization of (14) to aldehyde (15) was followed by a modified Wittig reaction to give the ethyl cinnamate derivative (16). Catalytic hydrogenation of (16) over Raney Nickel furnished aminoester (17) which was converted to the end product (18) by an analogous set of reactions as depicted in SCHEME 1. As previously indicated, compounds in this invention with substituents other than dichloro can be made in the same manner as depicted in Scheme 2 using the appropriate starting materials.

SCHEME 3

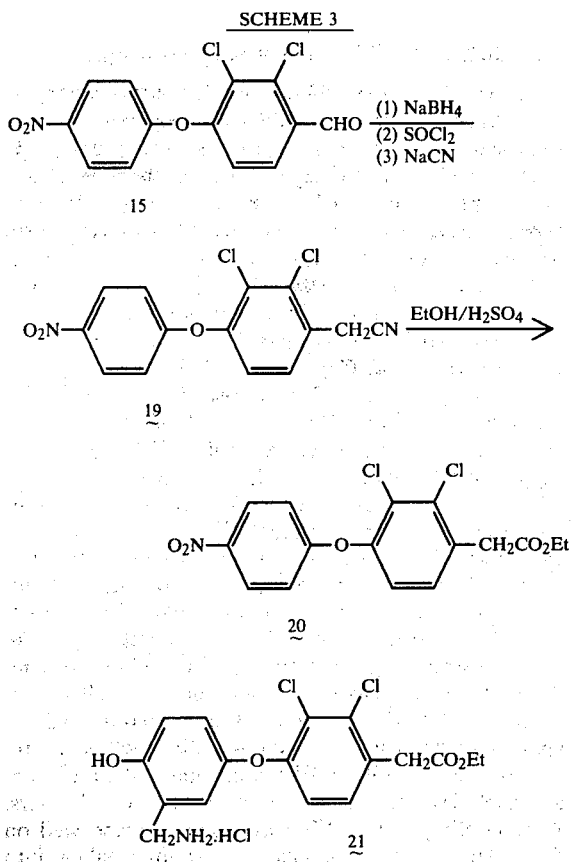

To prepare the substituted phenyl acetic acid ester of type (21), 2,3-dichloro-4-(p-nitrophenoxy)benzaldehyde (15) was reduced with NaBH$_4$ in ethanol to give the benzylic alcohol. The alcohol was treated with thionyl chloride in chloroform to provide the benzylic chloride. The chloride was converted to the benzylic nitrile (19) by refluxing with NaCN in ethanol. Hydrolysis of the nitrile gave the ethyl ester (20). Compound (20) was converted to the end product (21) by a series of reactions analogous to those depicted in SCHEMES 1 and 2.

EXAMPLE 1

Ethyl 2,3-dichloro-4-(4'-hydroxybenzoyl)phenoxyacetate 85.38 g. (0.25 mole) of 2,3-dichloro-4-(4'-hydroxybenzoyl)-phenoxyacetic acid, 34.5 g. (0.75 mole) of ethanol, and 100 ml. of ethylene dichloride, using 3.5 ml. of sulfuric acid as the catalyst were mixed and refluxed with stirring overnight according to the procedure of Clinton and Laskowski, J.A.C.S. 70 3135, 1948. The acid gradually went into solution. The reaction layer was cooled, separated and the organic layer washed successively with water, twice with KHCO$_3$ solution and finally with water. The dried ethylene dichloride was evaporated to dryness to give an oil which solidified to give 86 g. crude ester on trituration with pentane and filtering: m.p. 127°–9° (93% yield). This material was used without further purification in subsequent experiments.

EXAMPLE 2

Ethyl 2,3-dichloro-4-(4'-hydroxybenzyl)phenoxyacetate

To trifluoroacetic acid (50 ml.) under a nitrogen atmosphere was added 2.27 g. (0.06 mole) of NaBH$_4$ pellets over a period of 30 minutes at 5°. A solution of ethyl 2,3-dichloro-4-(4'-hydroxybenzoyl)phenoxyacetate (prepared as described in Example 1) (3 g., 0.0081 mole) in 30 ml. of methylene chloride was added dropwise at 15°–20° over a period of 20 minutes. The reaction mixture was stirred overnight at room temperature while the NaBH$_4$ pellets slowly dissolved. At this time the reaction mixture was poured into water and the resulting solution extracted with methylene chloride. The organic extract was washed with aqueous NaCL and dried over MgSO$_4$. Evaporation of the methylene chloride furnished a residue which was chromatographed on a silica gel column eluting with increasing amounts of methanol (MeOH) in CH$_2$Cl$_2$. There was obtained 2 g. of white solid, m.p. 102°–103°.

Analysis Calcd. for C$_{17}$H$_{16}$Cl$_2$O$_4$: C, 57.48; H, 4.54. Found: C, 57.57; H, 4.53.

EXAMPLE 3

Ethyl 2,3-dichloro-4-[(3'-chloroacetamidomethyl-4'-hydroxy)benzyl]phenoxyacetate 2-Chloro-N-(hydroxymethyl)acetamide (0.35 g., 0.0028 mole) was added, in small portions, to a stirred solution of ethyl 2,3-dichloro-4-(4'-hydroxybenzyl)-phenoxyacetate (1 g., 0.0028 mole) in 10 ml. of acetic acid and 1 ml. of concentrated sulfuric acid at 10°–15°. The mixture was stirred at room temperature overnight and poured in 150 ml. of ice water. The solid which formed was extracted into ethyl acetate and the resulting solution washed with aqueous NaCl and dried over MgSO$_4$. The residue obtained by evaporating the ethyl acetate was dissolved in 100 ml. of absolute ethanol and 0.6 ml. of concentrated sulfuric acid. After standing overnight at room temperature, the ethanol was partially evaporated under reduced pressure and the residue distributed between methylene chloride and aqueous NaCl. The organic layer was washed several times with aqueous NaCl, dried over MgSO$_4$, and evaporated. The crude ethyl ether was chromatographed on a silica gel column eluting with benzene/ethyl acetate (3:1) to give 0.67 g. of pure compound as a glass. This material was used as such for the next step.

EXAMPLE 4

Ethyl 2,3-dichloro-4-[(3'-aminomethyl-4'-hydroxy)benzyl]-phenoxyacetate hydrochloride A 2 g. sample of ethyl 2,3-dichloro-4-(3'-chloroacetamidomethyl-4'-hydroxy)benzyl phenoxyacetate (Example 3) was heated at reflux in 20 ml. of ethanol and 20 ml. of concentrated hydrochloric acid. After 4 hours, the mixture was cooled to room temperature and the reaction mixture was filtered. The resulting white solid was washed with 50% ethanol/ether and then dried. There was obtained 1.56 g. of pure material, m.p. 220°–222°.

Analysis Calcd. for C$_{18}$H$_2$OCl$_3$NO$_4$: C, 51.39; H, 4.79; N, 3.33. Found: C, 51.17; H, 4.88; N, 3.25.

EXAMPLE 5

Ethyl 2,3-dichloro-4-[(3'-aminomethyl-4'-hydroxy-5'-chloro)-benzyl]phenoxyacetate hydrochloride A mixture of 10 ml. of ethylene dichloride and 1.0 g. (0.00217 mole) of ethyl 2,3-dichloro-4-[(3'-chloroacetamidomethyl-4'-hydroxy)benzyl]phenoxyacetate was treated with 0.32 g. (0.0024 mole) of $SO_2Cl_2$. The mixture was heated at reflux for 2 hours and then evaporated to dryness under reduced pressure. The residue was chromatographed on silica gel eluting with $CH_2Cl_2/CH_3OH$ mixtures to give 1.15 g. of pure product. This material was used directly without further purification for the next step. The above sample (1.15 g.) was placed in 20 ml. of ethanol and 10 ml. of concentrated HCl and heated at reflux for 5 hours. After cooling the precipitated product was filtered and dried to give 850 mg. of hydrochloride salt, m.p. 234°–237°.

Analysis Calcd. for $C_{18}H_{19}Cl_4NO_4$: C, 47.50; H, 4.21; N, 3.08. Found: C, 47.50; H, 4.08; N, 3.05.

EXAMPLE 6

2,3-Dichloro-4-(p-nitrophenoxy)anisole

To a suspension of NaH (2.5 g., 0.052 mole of a 50% mineral oil suspension) in 60 ml. of DMF was added portionwise 2,3-dichloro-4-methoxyphenol (9.0 g., 0.047 mole) prepared as described by F. Dallacker and J. Van Wersch, Chem. Ber., 105, 3301 (1972). The mixture was stirred at room temperature under nitrogen for 15 minutes and then p-fluoronitrobenzene was rapidly added. The resulting mixture was heated at 100° for 2.5 hr., cooled to room temperature, and poured into ice water. The precipitate was filtered, washed with methanol and dried to give 13 g. of product, m.p. 165°–166°.

EXAMPLE 7

2,3-Dichloro-4-(p-nitrophenoxy)phenol

A mixture of 2,3-dichloro-4-(p-nitrophenoxy)anisole (13.5 g.) in 135 ml. of acetic acid and 80 ml. of 48% HBr was heated at reflux for 30 hours. After cooling, the product which had crystallized was filtered, washed with water and dried. There was obtained 11.6 g. of 2,3-dichloro-4-(p-nitrophenoxy)phenol, m.p. 147°–150°.

EXAMPLE 8

Ethyl 2,3-dichloro-4-(4'-nitrophenoxy)phenoxyacetate

A mixture of 2,3-dichloro-4-(p-nitrophenoxy)phenol (11.5 g., 0.038 mole), ethyl bromoacetate (9.51 g., 0.057 mole) and pulverized potassium carbonate (7.9 g., 0.057 mole) in 100 ml. of 2-butanone was heated at reflux for 2 hours. The reaction mixture was then filtered and the filtrate concentrated under reduced pressure. The residue was taken into $CH_2Cl_2$ and the resulting solution was washed with aqueous NaCl and dried over $MgSO_4$. Evaporation of the solvent was followed by trituration with hexane to furnish the solid product. Recrystallization from cyclohexane gave 12.5 g. of solid, m.p. 90°–91°.

Analysis Calcd. for $C_{16}H_{13}Cl_2NO_6$: C, 49.76; H, 3.39; N, 3.63. Found: C, 49.86; H. 3.28; N, 3.61.

EXAMPLE 9

Ethyl 2,3-dichloro-4-(4'-hydroxyphenoxy)phenoxyacetate

A solution of ethyl 2,3-dichloro-4-(4'-nitrophenoxy)phenoxyacetate (30 g.) in 1,000 ml. of ethanol was hydrogenated on the Parr apparatus over prewashed Raney nickel catalyst (12 g.). After the hydrogenation was complete, the catalyst was removed by filtration through celite and the filtrate mixed with ethanolic hydrogen chloride to form the amine salt. Evaporation of the ethanol then gave the hydrochloride salt (27.5 g.). To a stirred suspension of this salt in 425 ml. of aqueous $H_2SO_4$ (4 parts $H_2SO_4$ to 1 part $H_2O$) was added 5.1 g. (0.074 mole) of $NaNO_2$ in 16 ml. of H O, keeping the internal temperature at 5° or below. The resulting solution was stirred for 30 minutes at 0°–5° and then an additional 0.75 g. of $NaNO_2$ in 2 ml. of $H_2O$ was added. Stirring at 0°–5° was continued for 15 minutes and then 0.5 g. of $NaNO_2$ in 1 ml. of $H_2O$ was added. After an additional 1.25 hours stirring at 0°–5°, the slurry of the diazonium salt was slowly poured into a boiling mixture of $H_2O$ (990 ml.) and $H_2SO_4$ (595 ml.). The resulting clear solution was heated to boiling for 1.25 hours, then cooled and extracted with ethyl acetate (EtOAc). The organic extract was dried over $MgSO_4$ and evaporated to an oil which crystallized upon standing. Yield=21.5 g., m.p. 157°–61°. The crude 2,3-dichloro-4-(4'-hydroxyphenoxy)phenoxy acetic acid was dissolved in 300 ml. of absolute ethanol (EtOH) containing 1.0 ml. of concentrated $H_2SO_4$ and heated at reflux for 2.5 hours. After cooling, the EtOH was partially evaporated on the rotary evaporator and the residue taken into $CH_2Cl_2$ and washed with brine solution, aqueous $NaHCO_3$ and brine solution. Drying over $MgSO_4$ was followed by evaporation of the $CH_2Cl_2$ to give the solid ester. Recrystallization from cyclohexane/$CH_2Cl_2$ gave 17 g. of pure ethyl ester, m.p. 105°–106°.

EXAMPLE 10

Ethyl 2,3-dichloro-4-[(3'-chloroacetamidomethyl-4'-hydroxy)phenoxy]phenoxyacetate Using the procedure of Example 3, the title compound was prepared.

Materials used:
Ethyl-2,3-dichloro-4-(4'-hydroxyphenoxy)phenoxyacetate (22.9 g., 0.064 mole); 2-chloro-N-(hydroxymethyl)acetamide (8.65 g., 0.07 mole); acetic acid (210 ml.); sulfuric acid (21 ml.). Yield of product, 9 g., m.p. 84°–86°.

EXAMPLE 10(A)

Also isolated from the chromatographic purification of the title compound was the corresponding bis compound: Ethyl 2,3-dichloro-4-(3',5'-bis-dichloroacetamidomethyl-4'-hydroxy)phenoxy phenoxyacetate. This material was hydrolyzed in Example 11(A).

EXAMPLE 11

Ethyl 2,3-dichloro-4-[(3'-aminomethyl-4'-hydroxy)phenoxy]-phenoxyacetate, hydrochloride Using the procedure of Example 4, the title compound was prepared.

Materials used were:
Compound from Example 9, 0.66 g., 0.0014 mole; concentrated HCl, 5 ml.; ethanol, 5 ml. Yield of product, 0.47 g. (78%), m.p. 198°–201°.

Analysis Calcd. for $C_{17}H_{18}Cl_3NO_5$: C, 48.31; H, 4.29; N, 3.31. Found: C, 48.39; H, 4.32; N, 3.26.

EXAMPLE 11(A)

Bis-product, Ethyl 2,3-dichloro-4-(3',5'-bis-aminomethyl-4'-hydroxy)phenoxy phenoxyacetate, dihydrochloride was prepared as described above, m.p. 233° (dec.).

Analysis Calcd. for $C_{18}H_{22}Cl_4N_2O_4$: C, 44.29; H, 4.54; N, 5.74. Found: C, 44.59; H, 4.41; N, 5.52.

EXAMPLE 12

Ethyl 2,3-dichloro-4-[(3'-benzyloxycarboxamidomethyl-4'-hydroxy)phenoxy]phenoxyacetate To a stirred mixture of the compound of Example 11 (19 g.=0.045 mole) and benzyloxycarbonyloxysuccinimide (11.71 g.=0.047 mole) in 195 ml. of acetonitrile at 0°–5° was added all at once 4.7 g. (0.047 mole) of potassium bicarbonate in 50 ml. of $H_2O$. The ice-bath was removed and the reaction mixture was stirred for 1.5 hours. The clear solution was placed in a separatory funnel and the bottom water layer was drawn off and discarded. The remaining acetonitrile was evaporated under reduced pressure and the residue distributed between $CH_2Cl_2$ and aqueous NaCl. The organic layer was dried over $MgSO_4$ and evaporated to dryness. Trituration with hexane gave 22 g. of the N-CBZ derivative, m.p. 110°–112°.

EXAMPLE 13

2,3-Dichloro-4-[(3'-aminomethyl-4'-hydroxy)phenoxy]phenoxyacetamide, hydrobromide 11.05 g. of starting material (from Example 12) was dissolved in 200 ml. EtOH (dry, absolute) with about ½% $CH_2Cl_2$. Anhydrous $NH_3$ was passed in for 6 hours, and the mixture was allowed to stand, stoppered overnight. On disturbing the next day, the product ammonium salt suddenly crystallized. An excess of ether was added and precipitate collected. The precipitate was taken up in a minimum of EtOH and acidified by careful addition of a mixture of concentrated HCl and EtOH (1:1). Slow, dropwise addition to excess cold $H_2O$ produced a white precipitate, which was collected and dried and used directly in the next step. 9.37 g. of this compound was dissolved in 50 ml., 32% HBr in acetic acid (HOAc); gas was evolved followed by solidification of the product, over a period of about 10 minutes. 20 ml. additional HBr was added as a solvent and the mixture stirred for a few minutes longer, then diluted with 100 ml. dry ether. This was decanted into 200 ml. ether, stirred, filtered, and the precipitate taken up in methanol (MeOH). The MeOH was stripped off to remove traces of HBr and HOAc and the product was precipitated from MeOH by copious portionwise addition of ether. Yield, 6.74 g. (80.67%), m.p. 263°–264° C.

Analysis Calcd. for $C_{15}H_{15}BrCl_2N_2O_4$: C, 41.12; H, 3.45; N, 6.93. Found: C, 41.31; H, 3.50 N, 6.28.

EXAMPLE 14

2,3-Dichloro-4-[(3'-aminomethyl-4'-hydroxy-5'-chloro)phenoxy]phenoxyacetamide, hydrochloride The compound from Example 12 was chlorinated with $SO_2Cl_2$ as described in Example 5 and the resulting chloro derivative was treated by the procedure of Example 13 to give the title compound as the hydrobromide salt. This material was converted to the free base with ammonia in water and then the corresponding hydrochloride salt was prepared with hydrogen chloride gas, m.p. 235°–238°.

Analysis Calcd. for $C_{15}H_{14}Cl_4N_2O_4$: C, 42.09; H, 3.30; N, 6.54. Found: C, 41.81; H, 3.20; N, 6.47.

EXAMPLE 15

2,3-Dichloro-4-methoxybenzenethiol 2,3-Dichloro-4-methoxybenzenesulfonyl chloride was prepared as described by H. Zamarlik C. R. Acad. Sci. Paris, 273, 1756 (1971). A 9.5 g. sample of the sulfonyl chloride was dissolved in 100 ml. of anhydrous ether and added by dropwise addition to 3.12 g. of $LiAlH_4$ suspended in 80 ml. of ether. After stirring overnight at room temperature, the mixture was refluxed for 1 hour, cooled in an ice bath, and excess $LiAlH_4$ destroyed with water. Acidification with concentrated HCl was followed by extraction of the mixture with ether. The ethereal extract was dried and evaporated to dryness to give 6.4 g. of mercaptan, m.p. 84°–85.5°.

EXAMPLE 16

2,3-Dichloro-4-(p-nitrophenylsulfenyl)anisole

A mixture of 2,3-dichloro-4-methoxybenzenethiol (6.0 g., 0.024 mole), p-fluoronitrobenzene (3.04 ml., 0.029 mole) and anhydrous potassium carbonate (5.15 g., 0.038 mole) in 60 ml. of DMF was stirred at room temperature for 2 hours and then poured into water. The resulting solid product was filtered and washed well with ethanol to give 9.1 g. (96%), m.p. 236°–237°.

Analysis Calcd. for $C_{13}H_9Cl_2NO_3S$: C, 47.29; H, 2.75; N, 4.24. Found: C, 47.16; H, 2.71; N, 4.23.

EXAMPLE 17

2,3-Dichloro-4-(p-nitrophenylsulfenyl)phenetole

Using the procedure of Example 16 starting with 2,3-dichloro-4-mercaptophenetol, the title compound was prepared. It had m.p. 164°–165°. The 2,3-dichloro-4-mercaptophenetol was prepared as described in Example 15, starting with 2,3-dichlorophenetol.

EXAMPLE 18

2,3-Dichloro-4-(p-nitrophenylsulfenyl)phenol

A solution of the compound from Example 17 (10 g., 0.029 mole) in 400 ml. of methylene chloride was treated with 8.52 g. of $AlCl_3$ all at once at 0°. The reaction mixture was stirred overnight at room temperature and an additional 3.87 g. of $AlCl_3$ was added. Stirring was continued for an additional 3 hours at which time 3.87 g. of $AlCl_3$ was again added. After stirring for 4½ hours, the mixture was poured into 800 ml. of crushed ice and the precipitate filtered. The solid was washed with ethanol and dried to give 8.67 g. of product, m.p. 204°.

EXAMPLE 19

Ethyl 2,3-dichloro-4-(4'-nitrophenylsulfenyl)phenoxyacetate

This compound was prepared according to the procedure described in Example 8.

Materials:

6.99 g. (0.022 mole) compound from Example 18; 7.38 g. (0.044 mole) ethyl bromoacetate; 3.36 g. (0.024 mole) $K_2CO_3$. Yield: 7.85 g. (88%); m.p. 126°–127°.

Analysis Calcd. for $C_{16}H_{13}Cl_2NO_5S$: C, 47.78; H, 3.26; N, 3.48. Found: C, 47.61; H, 3.24; N, 3.56.

EXAMPLE 20

Ethyl 2,3-dichloro-4-(4'-hydroxyphenylsulfenyl)phenoxyacetate

The procedure described in Example 9 was used with the following changes: The hydrogenation catalyst employed was sulfided platinum on carbon (5%), rather than Raney nickel. The diazotization reaction was modified as follows: The aniline derivative from the hydrogenation (7.52 g., 0.02 mole) was dissolved in 50 ml. of concentrated $H_2SO_4$. To this solution was added 72 ml. of nitrosyl sulfuric acid (4.9 g. $NaNO_2$ dissolved in 72 ml. concentrated $H_2SO_4$) and the reaction mixture stirred overnight at room temperature. The mixture was then poured onto 850 ml. of ice and treated with urea to destroy excess nitrosyl sulfuric acid. The aqueous solution was added to a refluxing mixture of 1.7 g. of $Na_2SO_4$ dissolved in 25 ml. of concentrated $H_2SO_4$ and 25 ml. of water. After refluxing for 2 hours, the mixture was cooled and the solid product filtered and dried. There was obtained 6.46 g. of carboxylic acid (85%). The corresponding ester was prepared as described in Example 9.

EXAMPLE 21

Ethyl 2,3-dichloro-4-[(3'-chloroacetamidomethyl-4'-hydroxy)phenylsulfenyl]phenoxyacetate Using the procedure of Example 3, the title compound was prepared.

Materials used:

Compound from Example 20, 1.04 g. = 0.0028 mole; 2-chloro-N-(hydroxymethyl)acetamide, 0.378 g. = 0.003 mole; 10 ml. acetic acid; 1 ml. $H_2SO_4$. Yield of purified product, 1.1 g. (82%), m.p. 162°.

EXAMPLE 21(A)

Also isolated from the chromatographed purification of the title compound was the corresponding bis compound: Ethyl 2,3-dichloro-4-[(3',5'-bis-chloroacetamidomethyl-4'-hydroxy)phenylsulfenyl]-phenoxyacetate. This material was hydrolyzed in Example 22A.

EXAMPLE 22

Ethyl 2,3-dichloro-4-[(3'-aminomethyl-4'-hydroxy)phenylsulfenyl]phenoxyacetate, hydrochloride Using the procedure of Example 4, the title compound was prepared.

Materials used:

Compound from Example 21, 0.8 g. (0.00167 mole); concentrated HCl, 15 ml.; ethanol, 80 ml. Yield of product, 0.74 g.; m.p. 205° (dec).

Analysis Calcd. for $C_{17}H_{18}Cl_3NO_4S \cdot \frac{1}{2}H_2O$: C, 45.60; H, 4.28; N, 3.13. Found: C, 45.52; H, 4.08; N, 3.14.

EXAMPLE 22(A)

Methyl 2,3-dichloro-4-[(3',5'-bis-aminomethyl-4'-hydroxy)-phenylsulfenyl]phenoxyacetate, dihydrochloride The hydrolysis was carried out as above except methanol rather than ethanol was used. m.p. 240° (dec).

Analysis Calcd. for $C_{17}H_{20}Cl_4N_2O_4S$: C, 41.65; H, 4.11; N, 5.71. Found: C, 41.58; H, 4.02; N, 5.63.

EXAMPLE 23

2-{2,3-Dichloro-4-[(3'-aminomethyl-4'-hydroxy)-phenoxy]}phenoxyethanol, hydrochloride To a solution of ethyl 2,3-dichloro-4-[(3'-chloroacetamidomethyl-4'-hydroxy)phenoxy]phenoxyacetate (from Example 10) (4.88 g., 0.01 mole) in 50 ml. of ethanol was added 5.2 g. (0.136 mole) of $NaBH_4$ portionwise over a period of 60 minutes. After stirring for 3 hours at room temperature, the reaction mixture was poured into brine solution. The pH was adjusted to 3.5 with concentrated HCl and the solution extracted with $CH_2Cl_2$. After drying over $MgSO_4$ and evaporation of the $CH_2Cl_2$, the resulting residue was triturated with ether/$CH_2Cl_2$ to afford the pure phenoxyethanol derivative. Hydrolysis of this material was performed as described in Example 3: compound from above, 3.36 g., 0.008 mole; concentrated HCl, 30 ml.; ethanol, 80 ml.; yield 3 g., m.p. 181° (dec).

Analysis Calcd. for $C_{15}H_{16}Cl_3NO_4$: C, 46.73; H, 4.32; N, 3.66. Found: C, 46.71; H, 4.31; N, 3.58.

EXAMPLE 23(A)

The bis-compound described in Example 10A was reduced and hydrolyzed as described above to give 2-{2,3-dichloro-4-[(3',5'-bis-aminomethyl-4'-hydroxy)-phenoxy]}phenoxyethanol, dihydrochloride, m.p. 180° (dec).

Analysis Calcd. for $C_{16}H_{20}Cl_4N_2O_4$: C, 43.07; H, 4.52; N, 6.28. Found: C, 43.11; H, 4.45; N, 5.83.

EXAMPLE 24

Methyl 2,3-dichloro-4-[(3'-aminomethyl-4'-hydroxy)phenylsulfinyl]phenoxyacetate, hydrochloride The compound from Example 22 was protected on the amino group and phenol as follows: A solution of 1.19 g. (0.0027 mole) of the compound from Example 22 in 7 ml. of DMF was treated successively with 0.549 g. (0.0054 mole) of triethylamine and 0.651 g. (0.00298 mole) of di-tert-butyl-dicarbonate. The reaction was stirred at room temperature for 2½ hours and then poured into brine solution. Extraction with $CH_2Cl_2$ and evaporation gave 1.36 g. N-t-BOC derivative. This was dissolved in 5 ml. of $CH_2Cl_2$ and treated successively with 0.525 g. (0.004 mole) of diisopropylethyl amine and 0.506 g. (0.004 mole) of MEM-chloride. The mixture was stirred for one hour, the $CHCl_2$ solution was diluted with an additional 50 ml. of $CH_2Cl_2$, and the organic solution washed with brine solution. Evaporation furnished 1.55 g. of the MEM-ether. This material was oxidized to the sulfoxide by treating a solution in 3.6/ml. of pyridine and 0.3 ml. of H$_2$O with 0.698 g. (0.0025 mole) of iodobenzene dichloride. To this mixture was then added 50 ml. of H$_2$O and the reaction stirred overnight at room temperature. The supernatant liquid was decanted away from the gummy product which weighed 1.46 g. The gummy sulfoxide was allowed to stand overnight in 25 ml. of methanolic HCl. Evaporation to dryness furnished the desired product, 0.96 g., m.p. 224° (dec).

Analysis Calcd. for C$_{16}$H$_{16}$Cl$_3$NO$_5$S: C, 43.60; H, 3.66; N, 3.18. Found: C, 43.70; H, 3.77; N, 3.17.

EXAMPLE 25

2,3-Dichloro-4-(p-nitrophenoxy)benzaldehyde

A mixture of 31.76 g. (0.166 mole) of 2,3-dichloro-4-hydroxy-benzaldehyde prepared as described by J. B. Bicking, W. J. Holtz, L. S. Watson and E. J. Cragoe, Jr., J. Med. Chem. 19, 530 (1976), 14.5 g. (0.23 mole) of ethylene glycol, and 0.5 g. of p-toluenesulfonic acid in 300 ml. of benzene was heated in a Dean-Stark trap for 1 hour. The cooled solution was washed with water, dried and evaporated to give 33 g. of the acetal derivative, which was used without purification for the next step. A 32 g. (0.136 mole) sample of this acetal was allowed to react with 21.1 g. (0.15 mole) of p-fluoronitrobenzene and 7.19 g. (0.15 mole) of NaH in 160 ml. of DMF as described in Example 6. There was obtained 24 g. (49%) of the diphenyl ether product, m.p. 94°.

Analysis Calcd. for C$_{15}$H$_{11}$Cl$_2$NO$_5$: C, 50.58; H, 3.11; N, 3.93. Found: C, 50.91; H, 3.17; N, 4.03.

The acetal group in the above product was removed by stirring 81.8 g. (0.23 mole) of this material in 2000 ml. of acetone, 400 ml. of water and 80 ml. of H$_2$SO$_4$ for 48 hours. The acetone was evaporated and the residue filtered to give 47 g. (65%) of 2,3-dichloro-4-(p-nitrophenoxy)benzaldehyde.

EXAMPLE 26

Ethyl 2,3-dichloro-4-(p-nitrophenoxy)cinnamate

To a slurry of 4.8 g. (0.1 mole of a 50% mineral oil suspension) of NaH in 370 ml. of tetrahydrofuran was added 22.4 g. (0.1 mole) of triethylphosphonoacetate dropwise over a period of 15 minutes. This mixture was stirred for 15 minutes and then 30 g. (0.096 mole) of 2,3-dichloro-4-(p-nitrophenoxy)benzaldehyde was added portionwise in 15 minutes. After stirring for one hour, the reaction mixture was poured into water and the resulting product filtered and washed with EtOH to give 29.8 g. (81%) of the title compound, m.p. 145°-145.5°.

EXAMPLE 27

Ethyl 3-[2,3-dichloro-4-(p-hydroxyphenoxy)phenyl]propionate

A 30 g. sample of ethyl 2,3-dichloro-4-(p-nitrophenoxy)cinnamate was hydrogenated over 12 g. of Raney Nickel catalyst as described in Example 9 to give 28.6 g. (94%) of ethyl 3-2,3-dichloro-4-(p-aminophenoxy)phenyl propionate, m.p. 181°-183° dec. A 28.6 g. (0.07 mole) sample of this material was diazotized by the procedure detailed in Example 9 to give 22 g. of the title compound, m.p. 135°-136°.

EXAMPLE 28

Ethyl 3-{2,3-dichloro-4-[(3'-aminomethyl-4'-hydroxy)phenoxy]phenyl}propionate, hydrochloride The compound from Example 27 (23.7 g., 0.073 mole) was reacted with 8.97 g. (0.073 mole) of 2-chloro-N-(hydroxymethyl)acetamide as described in Example 3 to give 13.9 g. of the corresponding chloroacetamidomethyl derivative, m.p. 93°-94°. This material was hydrolyzed as described in Example 4 to give the title compound, m.p. 198°.

Analysis Calcd. for C$_{18}$H$_{20}$Cl$_3$NO$_4$: C, 51.39; H, 4.79; N, 3.33. Found: C, 51.28; H, 4.66; N, 3.45.

EXAMPLE 29

2,3-Dichloro-4-(p-nitrophenoxy)phenylacetonitrile

To a suspension of the compound from Example 25, (20.9 g., 0.067 mole) in 125 ml. of absolute ethanol was added 0.79 g. (0.021 mole) of NaBH$_4$. The mixture was stirred for 20 minutes at room temperature. The reaction mixture was diluted by careful addition of water and was then acidified with dilute HCl. The ethanol was evaporated under reduced pressure and the aqueous residue was extracted with methylene chloride. The organic solution was washed with brine, dried over Na$_2$SO$_4$ and evaporated to provide 20 g. of benzylic alcohol. This alcohol (20 g., 0.064 mole) was dissolved in 150 ml. of chloroform and 18.7 ml. of thionyl chloride was added. After the solution had been stirred for 5 hours at room temperature, the solvent was evaporated to give 21.1 g. of benzylic chloride. NMR (CDCl$_3$): 4.70 (2H, s, ArCH$_2$Cl). This chloride (21.1 g., 0.064 mole) was dissolved in 150 ml. of 95% ethanol and a solution of NaCN (3.74 g., 0.076 mole) in 25 ml. of water was added. The mixture was refluxed for 8 hours. The ethanol was evaporated and the aqueous residue was extracted with methylene chloride. The organic extract was washed with brine, dried over Na$_2$SO$_4$ and evaporated. The crude product was quickly passed through a short silica gel column using methylene chloride as the solvent. The desired product (16.6 g.) was obtained as a yellow solid. NMR (CDCl$_3$): 3.93 (2H, s, ArCH$_2$CN); IR (CHCl$_3$) 2250 cm$^{-1}$.

EXAMPLE 30

Ethyl 2,3-dichloro-4-(p-nitrophenoxy)phenylacetate

To a solution of 2,3-dichloro-4-(p-nitrophenoxy)phenyl acetonitrile (from Example 29) (6.5 g., 0.02 mole) in 15 ml. of 95% ethanol was added 5 ml. of concentrated H$_2$SO$_4$. The solution was refluxed for 24 hours. The ethanol was evaporated and the residue was diluted with water. The aqueous mixture was extracted with chloroform. The organic solution was washed with brine, dried over Na$_2$SO$_4$ and evaporated to provide 6.9 g. of the desired ethyl ester. NMR (CDCl$_3$): 3.87 (2H, s, ArCH$_2$CO$_2$Et); IR (CHCl$_3$) 1730 cm$^{-1}$.

EXAMPLE 31

Ethyl 2,3-dichloro-4-[(3'-aminomethyl-4'-hydroxy)phenoxy]phenyl acetate, hydrochloride A 25.5 g. sample of the compound from Example 30 was hydrogenated over 5 g. of Raney Nickel catalyst as described in Example 9 to give 26.5 g. of ethyl 2,3-dichloro-4-(p-aminophenoxy)phenyl acetate, hydrochloride. This material was diazotized as described in Example 9 to give ethyl 2,3-dichloro-4-(p-hydroxyphenoxy)phenylacetate. A 20.6 g., 10.060 mole) sample of this phenol was reacted with 7.82 g. (0.063 mole) of 2-chloro-N(hydroxymethyl)-acetamide as described in Example 3 to provide 6.28 g. of the corresponding chloroacetamidoethyl derivative. This material was hydrolyzed as described in Example 4 to give the title compound, m.p. 218°–219°.

Analysis Calcd. for $C_{17}H_{18}Cl_3NO_4$: C, 50.20; H, 4.47; N, 3.44. Found: C, 49.66; H, 4.36; N, 3.49.

EXAMPLE 32

3-{2,3-Dichloro-4-[(3'-aminomethyl-4'-hydroxy)-phenoxy]phenyl}propanol, hydrochloride The chloroacetamidomethyl derivative described in Example 28 was reduced with sodium borohydride as described in Example 23 with the exception that the reaction time was lengthened to 2 days and the quantity of sodium borohydride was increased 5-fold. The purified product was obtained by chromatography over silica gel eluting with benzene/ethyl acetate mixtures. Hydrolysis of the resulting propanol derivative as described in Example 3 gave the title compound, m.p. 194°–198° (dec.)

Analysis Calcd. for $C_{16}H_{18}Cl_3NO_3$: C, 50.75; H, 4.79; N, 3.70. Found: C, 50.79; H, 4.70; N, 3.64.

Diuretic screening of the compounds of this invention was conducted in normotensive rats using the following procedure:

Female rats (Sprague-Dawley), weighing 175–225 grams, are placed on a diet of sucrose and water overnight. DOCA (deoxycorticosterone acetate), is prepared as a 2.5% suspension in 0.2% hydroxypropyl methyl cellulose. Each rat is administered 0.2 ml. subcutaneously of the DOCA suspension two hours prior to treatment with the test compound.

The suspension or solutions of test compounds are prepared daily. The compounds are suspended in 0.2% hydroxypropyl methylcellulose (vehicle) and administered orally (by gavage) in 2 ml/kg of the rat's body weight. Immediately after dosing, each rat is loaded with an isotonic mixture of NaCl and KCl in the ratio of 40:60 equivalent to 3% of the rat's body weight.

The rats are placed in individual stainless steel metabolism cages. No food or water is allowed during the experiment. Urine is collected for a four hour period. The volume of urine is measured at four hours and an aliquot is taken for analysis of urine sodium and potassium concentrations. Sodium and potassium are measured using an Instrumentation Labs Digital Flame Photometer. The data are reported in: volume—ml.; sodium and potassium—meq/l.

Standard screening procedures involving the testing of two doses of each compound using 2 rats per dose in a 2-stage screening system. The normal screening doses are 30 and 100 mg/kg orally. Urinary excretions of sodium and potassium are expressed as meq/kg of the rat's body weight.

TABLE I

| Compound | R | $R_1$ | X | A | $ED_2$ |
|---|---|---|---|---|---|
| 1 | Cl | —CONH$_2$ | 0 | 0 | 1.5 |
| 2 | H | —CONH$_2$ | 0 | 0 | 2.2 |
| 3 | H | —COOC$_2$H$_5$ | 0 | 0 | 1.0 |
| 4 | H | —CH$_2$OH | 0 | 0 | 0.5 |
| 5 | —CH$_2$NH$_2$ | —COOC$_2$H$_5$ | 0 | 0 | 25 |
| 6 | —CH$_2$NH$_2$ | —CH$_2$OH | 0 | 0 | 34 |
| 7 | H | —COOC$_2$H$_5$ | S | 0 | 2 |
| 8 | —CH$_2$NH$_2$ | —COOCH$_3$ | S | 0 | 30 |
| 9 | H | —COOCH$_3$ | S=O | 0 | 23 |
| 10 | Cl | —COOC$_2$H$_5$ | CH$_2$ | 0 | 3.8 |
| 11 | H | —COOC$_2$H$_5$ | CH$_2$ | 0 | 16 |
| | Bumetanide | | | | 12 |
| 12 | H | —COOC$_2$H$_5$ | 0 | CH$_2$ | 25 |
| 13 | H | —COOC$_2$H$_5$ | 0 | bond | 21.5 |
| 14 | H | —CH$_2$OH | 0 | CH$_2$ | 14 |

Note Y is the same and is chloro.

The natriuretic potency of the compounds listed in the above table is reported as an $ED_2$. This is the oral dose (mg./kg.) necessary to produce an excretion in the 0–4 hour period after dosing, of 2-milliequivalents of Na+ per kilogram (meq/kg) in the rat urine.

What is claimed is:

1. A compound of the formula

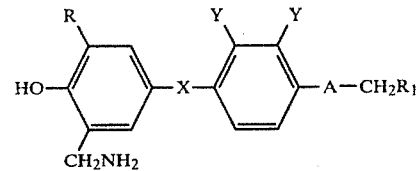

wherein R is hydrogen, loweralkyl, aminomethyl or halo; $R_1$ is carboxy, carboxyloweralkyl, aminocarbonyl, hydroxymethyl, anilinomethyl or aminomethyl; A is oxygen, CH$_2$, sulfur or a single bond; X is oxygen, CH$_2$, sulfur or sulfoxide; and Y is hydrogen, loweralkyl or halo and may be the same or different, and pharmaceutically acceptable salts thereof.

2. A compound of claim 1 wherein R is hydrogen, aminomethyl or halo, $R_1$ is carboxyloweralkyl, aminocarbonyl or hydroxymethyl, A is oxygen, CH$_2$ or a single bond, X is oxygen, CH$_2$ or sulfur, and Y is halo.

3. A compound of claim 2 wherein R is hydrogen, aminomethyl or chloro, $R_1$ is carboxyloweralkyl, aminocarbonyl or hydroxymethyl, A is oxygen, CH$_2$ or a single bond, X is oxygen, CH$_2$ or sulfur, and Y is chloro.

4. A compound of claim 3 wherein R is hydrogen or aminomethyl, $R_1$ is carboxymethyl, carboxyethyl or hydroxymethyl, A is oxygen, CH$_2$ or a single bond, X is oxygen or sulfur, and Y is chloro.

5. A compound of claim 3 wherein R is chloro, $R_1$ is aminocarbonyl, A is oxygen, X is oxygen, and Y is chloro.

6. A compound of claim 3 wherein R is hydrogen, $R_1$ is aminocarbonyl, A is oxygen, X is oxygen and Y is chloro.

7. A compound of claim 3 wherein R is hydrogen, $R_1$ is carboxyethyl, A is oxygen, X is oxygen and Y is chloro.

8. A compound of claim 3 wherein R is hydrogen, $R_1$ is hydroxymethyl, A is oxygen, X is oxygen and Y is chloro.

9. A compound of claim 3 wherein R is hydrogen, $R_1$ is carboxyethyl, A is oxygen, X is sulfur and Y is chloro.

10. A compound of claim 3 wherein R is chloro, $R_1$ is carboxyethyl, A is oxygen, X is —CH$_2$ and Y is chloro.

11. A method of increasing the urinary excretion of a patient comprising administering to a patient in need of such treatment a therapeutically effective amount of a diuretic agent of the formula

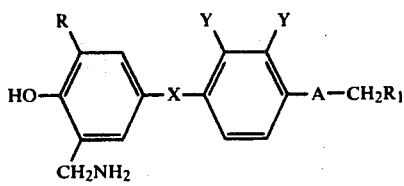

wherein R is hydrogen, loweralkyl, aminomethyl or halo; $R_1$ is carboxy, carboxyloweralkyl, aminocarbonyl, hydroxymethyl, anilinomethyl or aminomethyl; A is oxygen, $CH_2$, sulfur or a single bond; X is oxygen, $CH_2$, sulfur or sulfoxide; and Y is hydrogen, loweralkyl or halo and may be the same or different, and pharmaceutically acceptable salts thereof.

12. The method of claim 11 wherein R is hydrogen, aminomethyl or halo, $R_1$ is carboxyloweralkyl, aminocarbonyl or hydroxymethyl, A is oxygen, $CH_2$ or a single bond, X is oxygen, $CH_2$ or sulfur, and Y is halo.

13. The method of claim 12 wherein R is hydrogen, aminomethyl or chloro, $R_1$ is carboxyloweralkyl, aminocarbonyl or hydroxymethyl, A is oxygen, $CH_2$ or a single bond, X is oxygen, $CH_2$ or sulfur, and Y is chloro.

14. The method of claim 13 wherein R is hydrogen or aminomethyl, $R_1$ is carboxymethyl, carboxyethyl or hydroxymethyl, A is oxygen, $CH_2$ or a single bond, X is oxygen or sulfur, and Y is chloro.

15. The method of claim 13 wherein R is chloro, $R_1$ is aminocarbonyl, A is oxygen, X is oxygen, and Y is chloro.

16. The method of claim 13 wherein R is hydrogen, $R_1$ is aminocarbonyl, A is oxygen, X is oxygen and Y is chloro.

17. The method of claim 13 wherein R is hydrogen, $R_1$ is carboxyethyl, A is oxygen, X is oxygen and Y is chloro.

18. The method of claim 13 wherein R is hydrogen, $R_1$ is hydroxymethyl, A is oxygen, X is oxygen and Y is chloro.

19. The method of claim 13 wherein R is hydrogen, $R_1$ is carboxyethyl, A is oxygen, X is sulfur and Y is chloro.

20. The method of claim 13 wherein R is chloro, $R_1$ is carboxyethyl, A is oxygen, X is —$CH_2$ and Y is chloro.

21. A pharmaceutical composition useful as a diuretic which comprises an effective amount of a compound of the formula

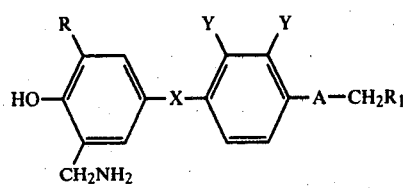

wherein R is hydrogen, loweralkyl, aminomethyl or halo; $R_1$ is carboxy, carboxyloweralkyl, aminocarbonyl, hydroxymethyl, anilinomethyl or aminomethyl; A is oxygen, $CH_2$, sulfur or a single bond; X is oxygen, $CH_2$, sulfur or sulfoxide; and Y is hydrogen, loweralkyl or halo and may be the same or different, and pharmaceutically acceptable salts thereof, and a pharmaceutically acceptable carrier.

22. The composition of claim 21 wherein R is hydrogen, aminomethyl or halo, $R_1$ is carboxyloweralkyl, aminocarbonyl or hydroxymethyl, A is oxygen, $CH_2$ or a single bond, X is oxygen, $CH_2$ or sulfur, and Y is halo.

23. The composition of claim 22 wherein R is hydrogen, aminomethyl or chloro, $R_1$ is carboxyloweralkyl, aminocarbonyl or hydroxymethyl, A is oxygen, $CH_2$ or a single bond, X is oxygen, $CH_2$ or sulfur, and Y is chloro.

24. The composition of claim 23 wherein R is hydrogen or aminomethyl, $R_1$ is carboxymethyl, carboxyethyl or hydroxymethyl, A is oxygen, $CH_2$ or a single bond, X is oxygen or sulfur, and Y is chloro.

25. The composition of claim 23 wherein R is chloro, $R_1$ is aminocarbonyl, A is oxygen, X is oxygen, and Y is chloro.

26. The composition of claim 23 wherein R is hydrogen, $R_1$ is aminocarbonyl, A is oxygen, X is oxygen and Y is chloro.

27. The composition of claim 23 wherein R is hydrogen, $R_1$ is carboxyethyl, A is oxygen, X is oxygen and Y is chloro.

28. The composition of claim 23 wherein R is hydrogen, $R_1$ is hydroxymethyl, A is oxygen, X is oxygen and Y is chloro.

29. The composition of claim 23 wherein R is hydrogen, $R_1$ is carboxyethyl, A is oxygen, X is sulfur and Y is chloro.

30. The composition of claim 23 wherein R is chloro, $R_1$ is carboxyethyl, A is oxygen, X is —$CH_2$ and Y is chloro.

* * * * *